(12) United States Patent
Osawa (10) Patent No.: US 8,465,429 B2
(45) Date of Patent: Jun. 18, 2013

(54) ULTRASONIC DIAGNOSTIC APPARATUS

(75) Inventor: Atsushi Osawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 156 days.

(21) Appl. No.: 13/016,331

(22) Filed: Jan. 28, 2011

(65) Prior Publication Data
US 2011/0218441 A1 Sep. 8, 2011

(30) Foreign Application Priority Data
Mar. 2, 2010 (JP) .................................. 2010-045608

(51) Int. Cl.
*A61B 8/00* (2006.01)
(52) U.S. Cl.
USPC ............................ 600/445; 600/444; 600/459
(58) Field of Classification Search
USPC .......................................... 600/444, 445, 459
See application file for complete search history.

(56) References Cited

U.S. PATENT DOCUMENTS

| | | | |
|---|---|---|---|
| 6,888,640 B2 * | 5/2005 | Spina et al. ................... | 356/601 |
| 2007/0193354 A1 * | 8/2007 | Felix et al. ................. | 73/514.32 |
| 2007/0239006 A1 * | 10/2007 | Kamiyama et al. ........... | 600/437 |
| 2007/0239020 A1 * | 10/2007 | Iinuma et al. ................. | 600/459 |
| 2008/0221454 A1 * | 9/2008 | Davidsen ..................... | 600/459 |

FOREIGN PATENT DOCUMENTS

| | | |
|---|---|---|
| JP | 2007-301070 A | 11/2007 |
| JP | 2009-225904 A | 10/2009 |

OTHER PUBLICATIONS

Translation of JP 2009-225904 A.*

* cited by examiner

*Primary Examiner* — Unsu Jung
*Assistant Examiner* — Rajeev Siripurapu
(74) *Attorney, Agent, or Firm* — Sughrue Mion, PLLC (57) ABSTRACT

In an examination section of an ultrasonic diagnostic apparatus, an ultrasonic transducer (UT) unit, a shape measurement unit, and a belt conveyor for moving the UT unit and the shape measurement unit parallel to an object to be viewed are provided. The UT unit has an UT array constituted of five ultrasonic transducers UTa to UTe arranged on a curved convex surface. The UT unit performs ultrasonic scanning of the object C to be viewed. The shape measurement unit has a laser light source and a light receiver, and measures a shape of the object C to be viewed. Based on the result of the shape measurement, a main controller of a processor selectively drives the UT, which could apply the ultrasonic wave vertically to the object C to be viewed, among the UTa to UTe, according to the moved position of the UT unit.

11 Claims, 8 Drawing Sheets

ULTRASONIC DIAGNOSTIC APPARATUS

BACKGROUND OF THE INVENTION

1. Field of the Invention

The present invention relates to an ultrasonic diagnostic apparatus that performs ultrasonic scanning based on a shape of an object to be viewed of a subject.

2. Description of the Related Art

An ultrasonic diagnostic apparatus in which an object to be viewed, for example a breast, of a patient's body as a subject is examined by performing ultrasound examination for breast cancer screening has recently been known. In such ultrasonic diagnostic apparatus, various techniques are tried in order to apply ultrasonic waves to the breast having a curved surface shape so that high quality ultrasonic images can be obtained.

In Japanese Patent Laid-Open Publication Nos. 2007-301070 and 2009-225904, an ultrasonic diagnostic apparatus in which a breast is immersed in warm water or the like, and an ultrasonic transducer unit or an ultrasonic probe is mechanically moved inside the warm water to perform ultrasonic scanning of the breast is disclosed. In the Japanese Patent Laid-Open Publication Nos. 2007-301070 and 2009-225904, the breast is pre-scanned to obtain shape information thereof by performing ultrasonic scanning or laser scanning of the breast. Based on the scanning result, the ultrasonic transducer unit or the ultrasonic probe is lifted up and down, moved, or tilted to apply the ultrasonic waves vertically to the breast.

According to the inventions disclosed in the Japanese Patent Laid-Open Publication Nos. 2007-301070 and 2009-225904, a mechanism for lifting up and down or tilting the ultrasonic transducer unit or the ultrasonic probe is needed, which makes the structure of the apparatus complex. As a result, there arises a problem that costs for assembly, components and maintenance increase. According to this, commercialization of the inventions disclosed in the Japanese Patent Laid-Open Publication Nos. 2007-301070 and 2009-225904 has been difficult in view of cost.

SUMMARY OF THE INVENTION

An object of the present invention is to provide an ultrasonic diagnostic apparatus enabling acquisition of relatively high quality ultrasonic images with simple configuration.

In order to achieve the above and other objects, an ultrasonic diagnostic apparatus according to the present invention includes a shape measurement section, an ultrasonic transducer array, a moving mechanism, and a drive controller. The shape measurement section measures a shape of an object to be viewed of a subject. The ultrasonic transducer array includes a plurality of ultrasonic transducers arranged on a curved surface. Each ultrasonic transducer transmits an ultrasonic wave to the object to be viewed and receives an echo of the ultrasonic wave from the object to be viewed. The moving mechanism moves the ultrasonic transducer array in a horizontal direction with respect to the object to be viewed. Based on the shape information of the object to be viewed obtained by the shape measurement section, the drive controller selectively drives the ultrasonic transducer which probably applies the ultrasonic wave vertically to the object to be viewed among the plurality of ultrasonic transducers according to the moved position of the ultrasonic transducer array.

It is preferable that the plurality of ultrasonic transducers of the ultrasonic transducer array is arranged on the curved convex surface. Note that the surface on which the ultrasonic transducers are arranged is not limited to the curved convex surface, and may be the curved concave surface. The curved surface may be a multiangular shape in cross-section formed by connecting plural flat surfaces tilted by different angles.

The shape measurement section measures the shape of the object to be viewed in a noncontact manner. Specifically, the shape measurement section includes a light projector for applying light to the object to be viewed and a light receiver for receiving the reflected light from the object to be viewed, and calculates shape information of the object to be viewed based on an output of the light receiver. The light projector and the light receiver move ahead of the ultrasonic transducers.

It is preferable that the ultrasonic transducer is a semiconductor device. The semiconductor device is specifically a cMUT (capacitive micromachined ultrasonic transducer) or a pMUT (piezoelectric micromachined ultrasonic transducer).

It is preferable that an ultrasonic wave transmission medium is mediated between the object to be viewed and the ultrasonic transducer array.

It is preferable that the ultrasonic diagnostic apparatus further includes a water tank and an elastic sheet. The water tank stores liquid, and the ultrasonic transducer array moves inside the water tank. The elastic sheet covers a surface of the liquid, and the subject is made into contact with the elastic sheet. The light projector and the light receiver are placed inside the water tank and move ahead of the ultrasonic transducers.

It is preferable that the object to be viewed includes a soft tissue such as breasts, abdomen, thyroid gland, carotid artery and joints (elbow, knee, etc.).

According to the present invention, the ultrasonic transducer array composed of the plurality of the ultrasonic transducers arranged on the curved surface is moved horizontally with respect to the object to be viewed, and at the same time, the ultrasonic transducer which probably applies the ultrasonic wave vertically to the object to be viewed is selectively driven in sequence, based on the result of the shape measurement of the object to be viewed. Owing to this, the ultrasonic images of high quality can be obtained with simple configuration.

BRIEF DESCRIPTION OF THE DRAWINGS

For more complete understanding of the present invention, and the advantage thereof, reference is now made to the following descriptions taken in conjunction with the accompanying drawings, in which.

DESCRIPTION OF THE PREFERRED EMBODIMENTS

Figure 1:
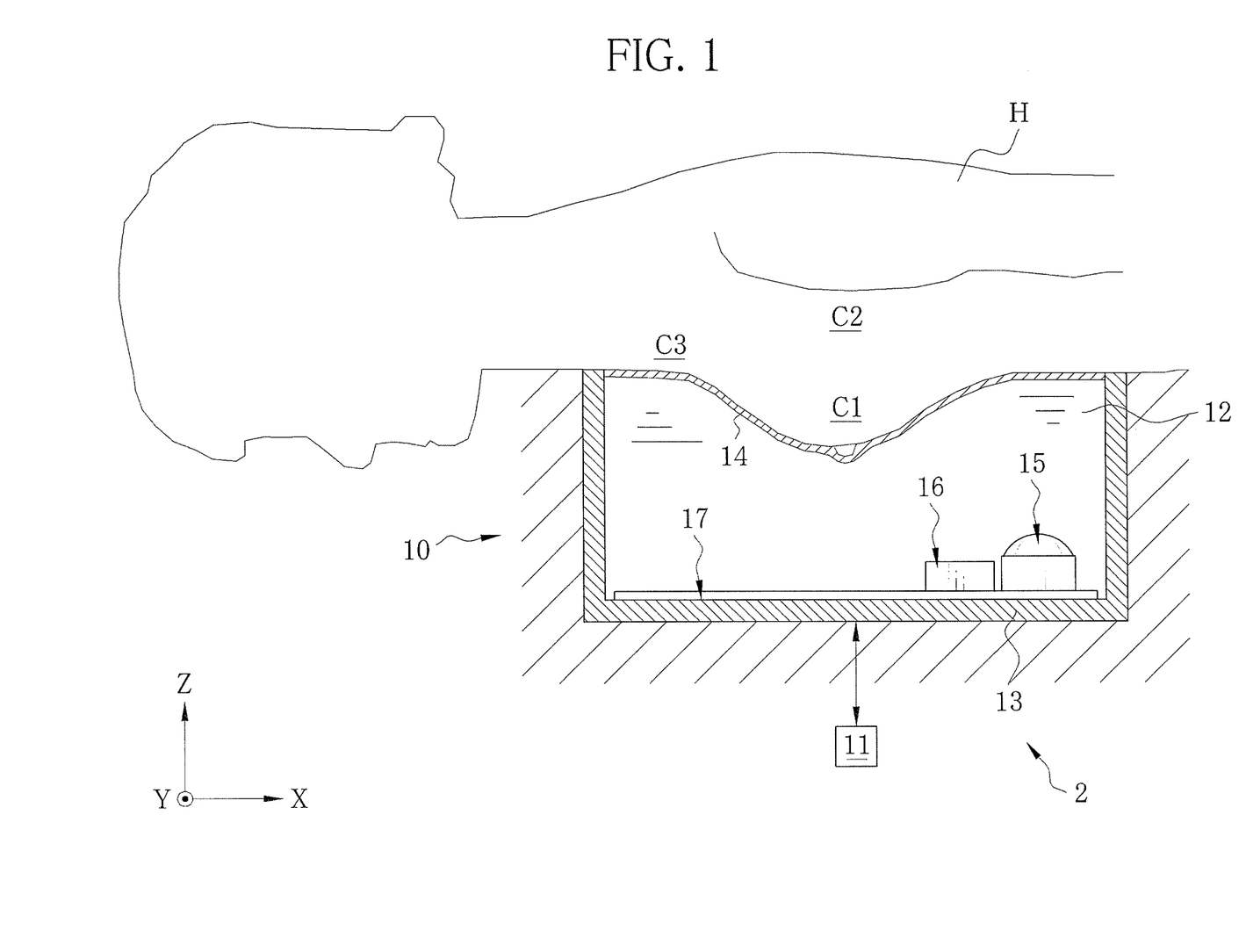
FIG. 1 is a schematic block diagram illustrating an ultrasonic diagnostic apparatus of the present invention.

In FIG. 1, an ultrasonic diagnostic apparatus 2 is for obtaining ultrasonic images of a breast C1, an axillary cavity (armpit) C2 surrounding the breast C1, and an area under the collarbone C3 (hereinafter, collectively referred to as the object C to be viewed) which are areas where breast cancer is developed in a body of a patient H as a subject. The ultrasonic diagnostic apparatus 2 is constituted of an examination section 10 and a processor 11. The patient's body H is laid on her stomach on a bed (not shown), and kept quiet with one breast C1 faced the examination section 10 which is provided inside the bed. In explanation below, a longitudinal direction of the bed is defined as an X direction, a direction orthogonal to the X direction is defined as a Y direction (both X and Y directions correspond to a horizontal direction), and a vertical direction is defined as a Z direction.

The examination section 10 has a water tank 13 and an elastic sheet 14. In the water tank 13, for example, warm water 12 is filled. The elastic sheet 14 covers over a top opening of the water tank 13. The water tank 13 is large enough to accommodate the object C to be viewed. The elastic sheet 14 is made of a material capable of transmitting ultrasonic waves, and is transformed to follow the shape of the object C to be viewed due to its weight when the object C to be viewed is placed thereon.

In the water tank 13, an ultrasonic transducer (hereinafter, abbreviated to UT) unit 15, a shape measurement unit 16, a belt conveyor 17, and the like are provided. An electric system of each component is located in a space where water-tightness is ensured, and electrically connected to the external processor 11 by a distributing cable (not shown) through a seal opening (not shown) formed on the water tank 13.

Figure 2:
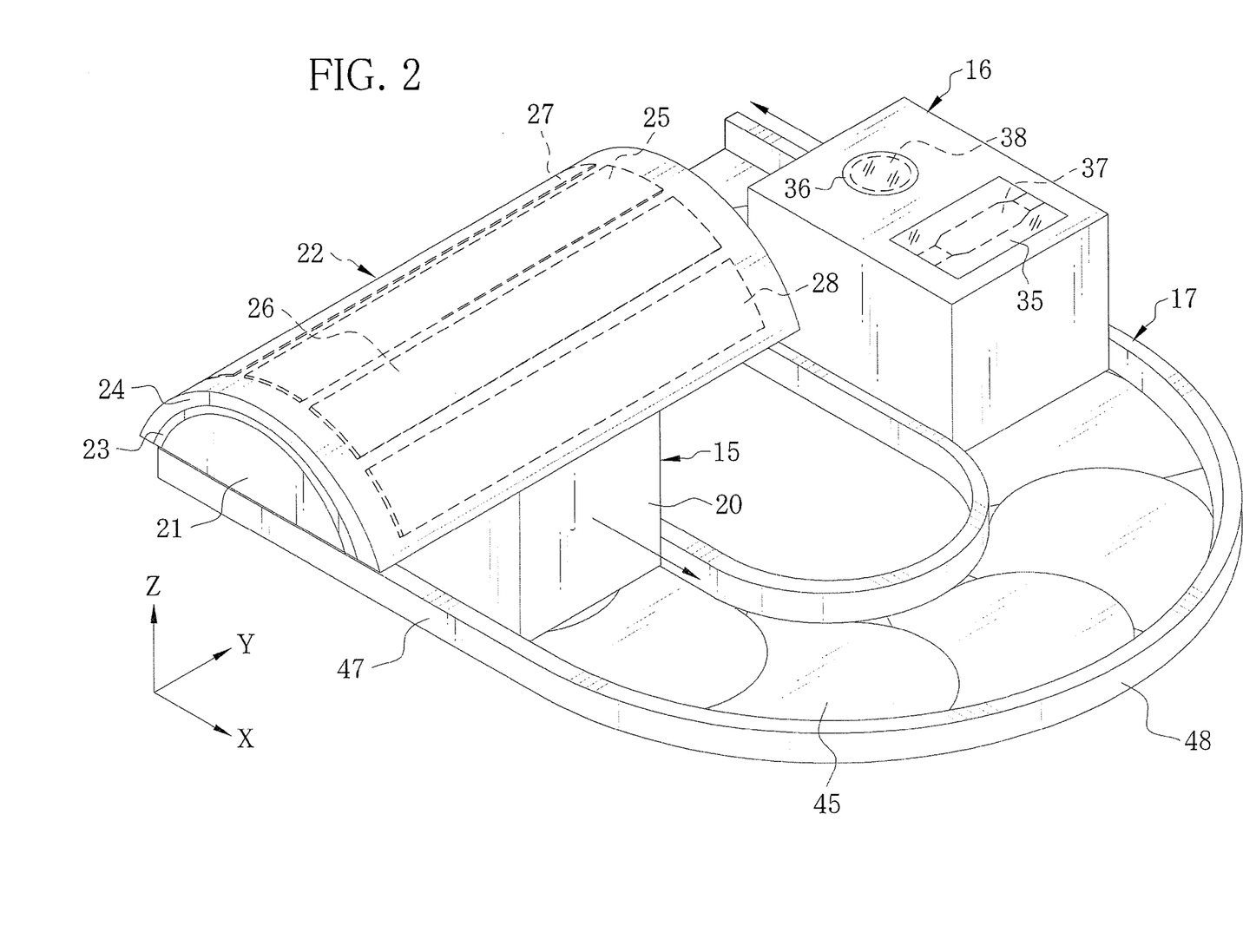
FIG. 2 is an external perspective view illustrating a substantial part of an examination section.

In FIG. 2, the UT unit 15 includes a cuboid base 20, a backing material 21 attached to the base 20, an UT array 22 provided on the backing material 21, and the like. The backing material 21 has a convex circular arc cross-section parallel to the XZ plane, and is formed to extend in the Y direction, that is, projecting from either end in the Y direction. On top of the UT array 22 is provided an acoustic matching layer 23 for alleviating difference in acoustic impedance between the ultrasonic transducer array 22 and the patient's body H. On top of the acoustic matching layer 23 is attached an acoustic lens 24 for concentrating the ultrasonic waves emitted from the UT array 22 onto the object C to be viewed. In addition, the UT unit 15 is provided with a wiring substrate and the like.

Figure 6:
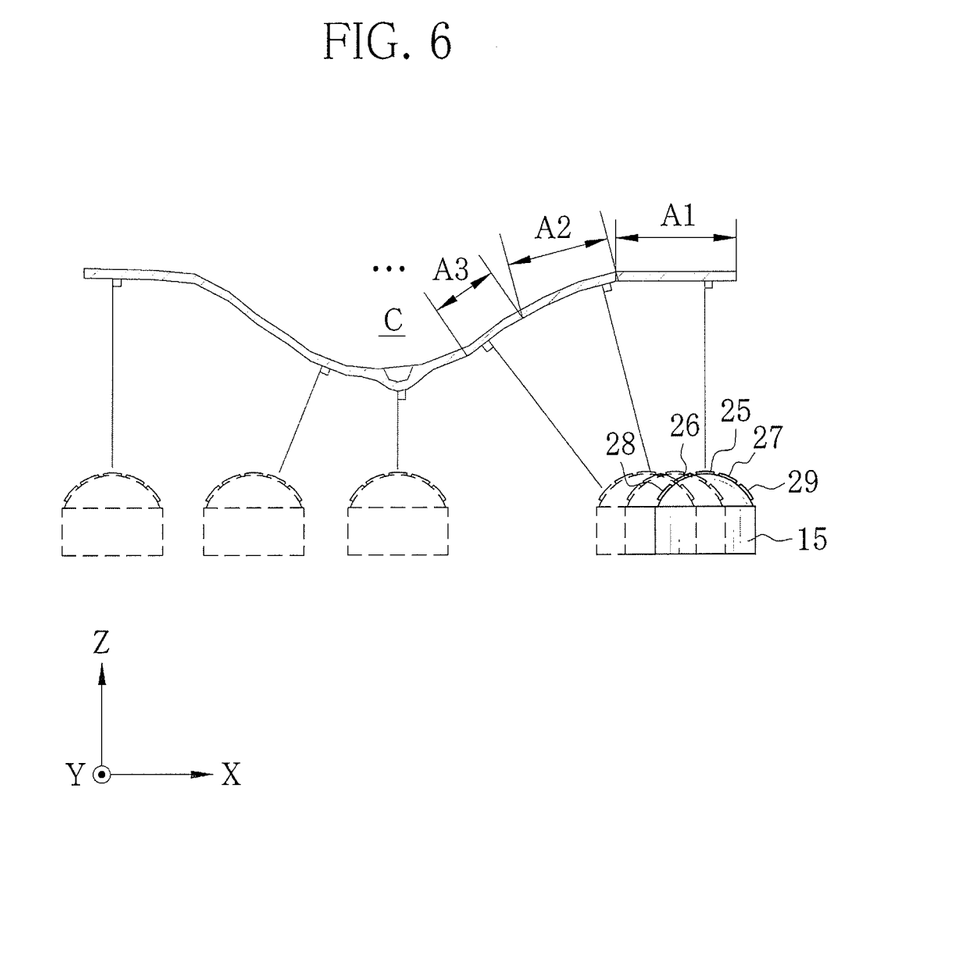
FIG. 6 is an explanatory view illustrating a drive example of the ultrasonic transducer array.

The UT array 22 has five UTs: UTa 25, UTb 26, UTc 27, UTd 28 and UTe 29 (UTe 29 is shown in FIG. 6) each of which having an approximately rectangle shape. The UTs 25 to 29 are arranged in one-dimensional array by a predetermined pitch. Although the material of the UT is not specifically regulated, the UT is made of, for example, a PZT-based piezoelectric ceramic thick film.

The UTa 25 to UTe 29 are attached to the curved surface of the backing material 21 such that the UTs 25 to 29 are aliened in the X direction. A length (length in the Y direction in FIG. 2) of each UT is equal to a combination of a width of the base 20 (width of a first straight running path 47 of the belt conveyor 17) and a space between the adjacent first straight running paths 47. That is, the UT is projecting from the base 20 at either end in the Y direction for the length same as half the width of the space between the adjacent first straight running paths 47.

The UTa 25 is located at the top of the curved convex surface of the backing material 21, and forms an angle of approximately 0 degree with the XY plane (approximately parallel to the XY plane). The UTb 26 and UTc 27 each of which is adjacent to the UTa 25 are located on a convex slope, such as a shoulder, of the curved convex surface of the backing material 21, and form an angle of approximately 30 degrees with the XY plane. The UTd 28 and UTe 29 are located at the bottom, at each end of the curved convex surface of the backing material 21, and form an angle of approximately 60 degrees with the XY plane.

The shape measurement unit 16 measures a three-dimensional (3D) shape of the object C to be viewed, and has a cuboid shape approximately same size as the base 20 of the UT unit 15. On top of the shape measurement unit 16 is provided light projecting window 35 and light receiving window 36 through which laser light passes. A laser light source 37 and a light receiver 38 are provided at the back of the light projecting window 35 and the light receiving window 36, respectively. The laser light source 37 is constituted of, for example, infrared semiconductor laser elements, and emits inflated laser light to the object C to be viewed. The light receiver 38 is constituted of, for example, CMOS image sensors, and receives the laser light reflected on the object C to be viewed.

Figure 3:
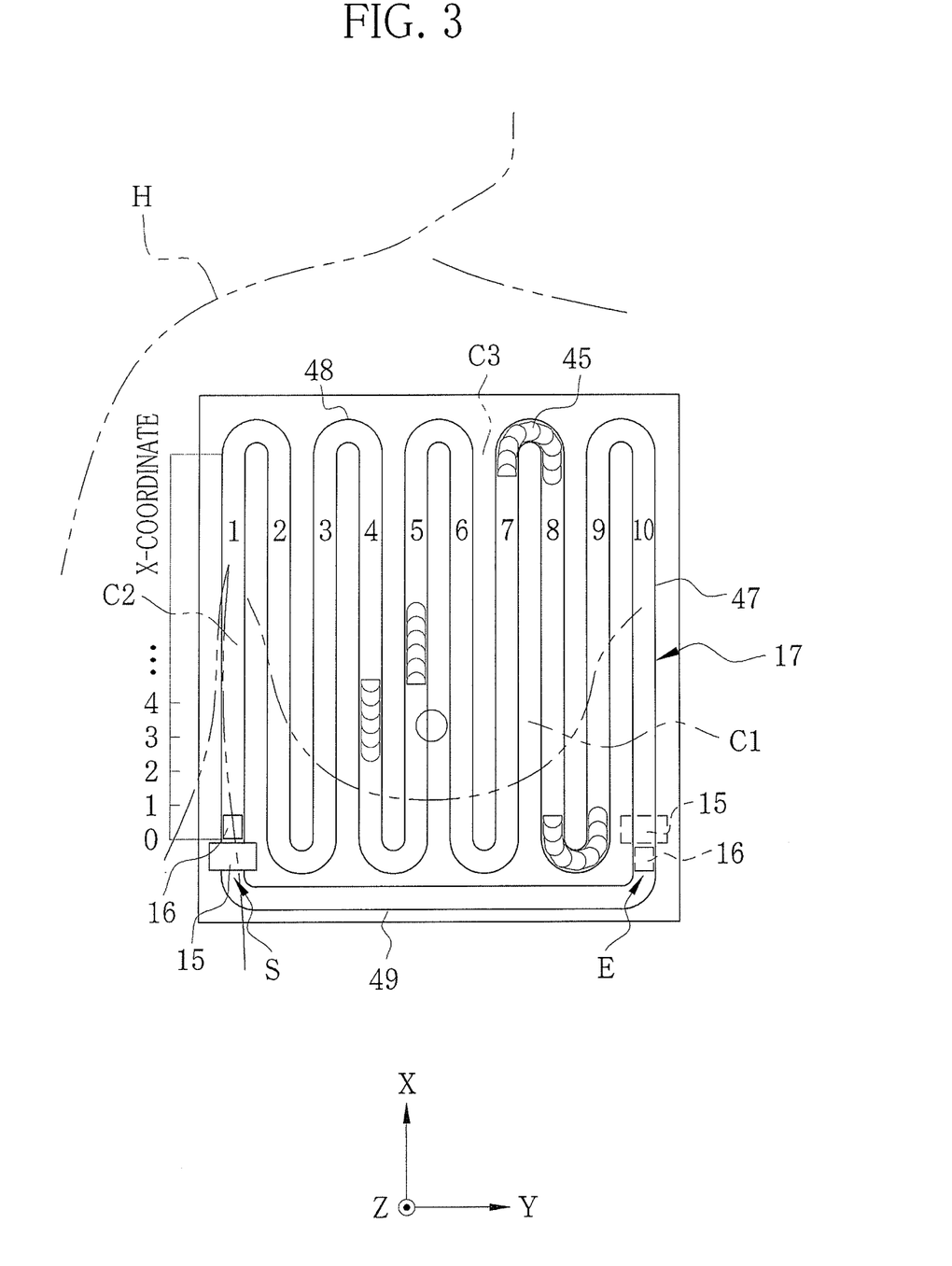
FIG. 3 is a plan view illustrating scanning area and trajectory of an ultrasonic transducer array.
Figure 4:
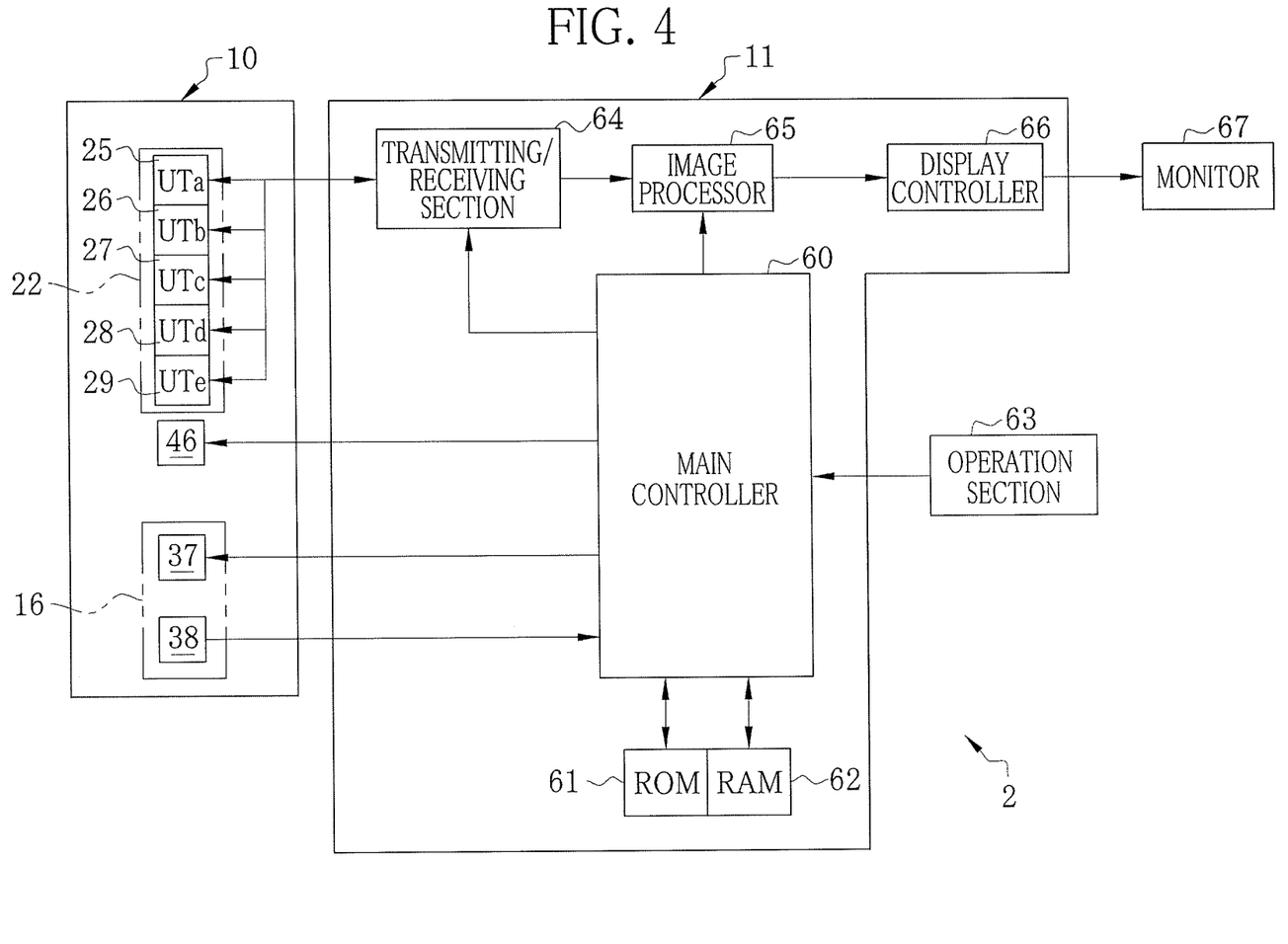
FIG. 4 is a block diagram illustrating an electrical configuration of the ultrasonic diagnostic apparatus.

The belt conveyer 17 is a conveyance device for moving a cyclic crescent top chain forward in a cyclic manner by driving a motor 46 (see FIG. 4). As shown in FIG. 3, the belt convey 17 has the first straight running paths 47, curved running paths 48 and a second straight running path 49. The first straight running paths 47 extending in the X direction are aligned in plural lines (for example, 10 lines) in the Y direction. The curved running paths 48 connect the adjacent two straight running paths 47. The second straight running path 49 connects a running start point S and a running end point E of each unit 15, 16 and extends in the Y direction. Each unit 15, 16 is placed on the belt conveyor 17 and moves along the belt conveyor 17, with the shape measurement unit 16 always ahead of the UT unit 15, in a zig-zag manner on the XY plane at constant speed. Owing to this, shape measurement and ultrasonic scanning of the object C to be viewed can be made.

In FIG. 4, a main controller 60 takes overall control of the operations of the processor 11. The main controller 60 is connected to each component of the processor 11 via a data bus, an address bus, or a control wire (not shown). A ROM 61 stores various programs (OS, application programs, etc.) and data (graphic data, etc.) for operating the processor 11. The main controller 60 reads out the necessary programs and data from the ROM 61 and develops them in a RAM 62, which is a work memory, to sequentially operate the read programs. The main controller 60 receives operation signals from an operation section 63, and executes the corresponding operation by each component.

Figure 5:
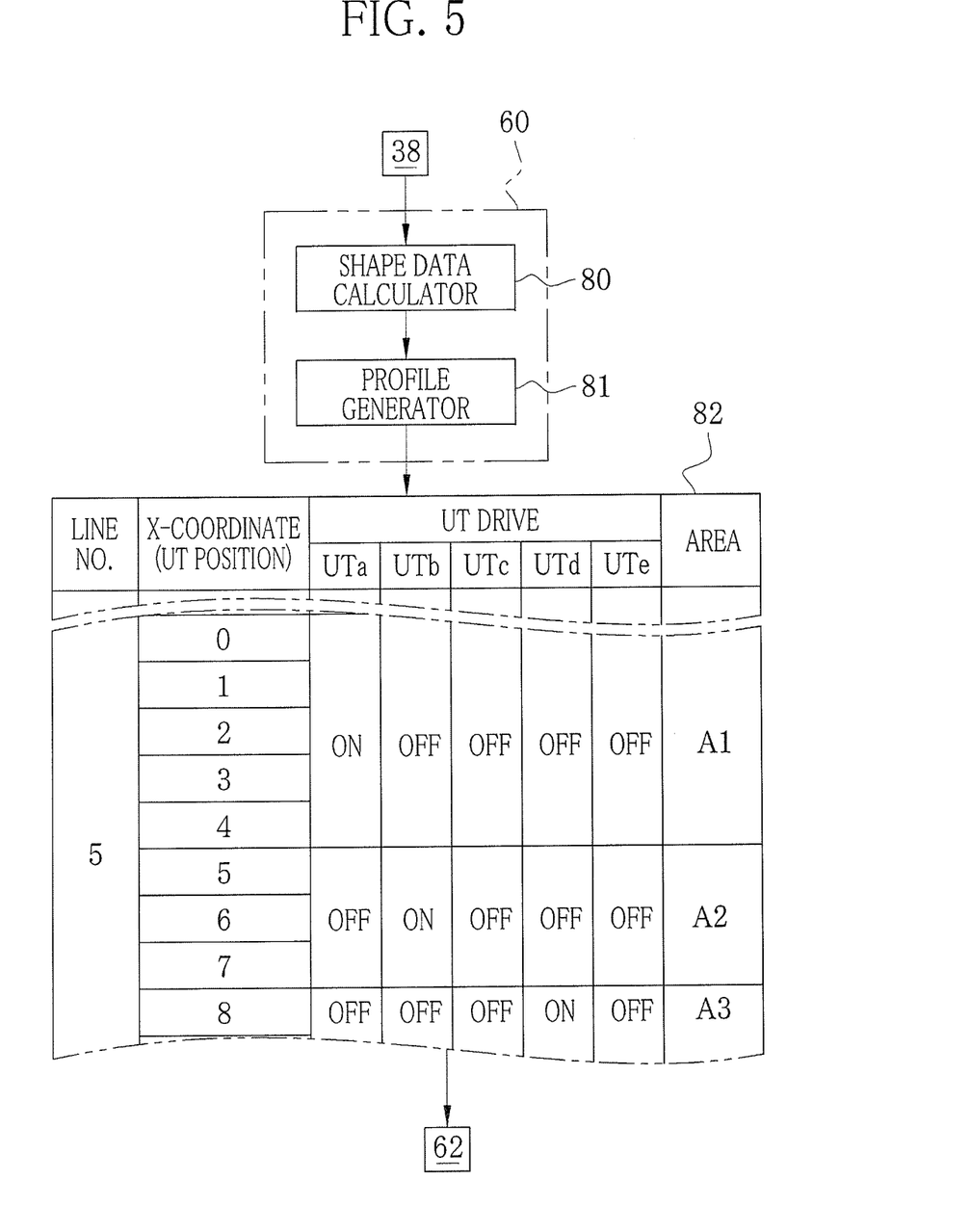
FIG. 5 is a block diagram illustrating a configuration of a main controller and an example of a profile.

The light receiver 38 of the shape measurement unit 16 is connected to the main controller 60. As shown in FIG. 5, a shape data calculator 80 and a profile generator 81 are built in the main controller 60 once the program in the ROM 61 is executed. The shape data calculator 80 calculates shape data representing 3D shape of the object C to be viewed, based on the triangulation, from an output of the light receiver 38. Based on the shape data calculated by the shape data calculator 80, the profile generator 81 generates a profile 82 representing drive control procedures of the UT array 22.

The profile 82 regulates which UTa 25 to UTe 29 is driven to perform the ultrasonic scanning for every line No. and X-coordination (see FIG. 3) of the first straight running paths 47. The profile generator 81 finds out the UT which can vertically apply the ultrasonic wave to the object C to be viewed according to the shape data for each area A1, A2, A3, and more (see FIG. 6). Specifically, the angle between the corresponding area and the XY is obtained from the shape data, and the UT whose tilt angle is closest to the obtained angle is selected.

For example, the area A1 shown in FIG. 6 is approximately parallel to the X direction, that is, the area A1 forms an angle of approximately 0 degree with the XY plane. Therefore, the UTa 25 is selected to drive. Similarly, the area A2 and the area A3 form the angles of approximately 30 degrees and 60 degrees, respectively. Therefore, the UTb 26 and the UTd 28 are selected, respectively. The profile generator 81 performs such UT selection for each line and X-coordination of the first straight running paths 47, and thereby producing the profile 82 covering the whole object C to be viewed. In producing the profile 82, it is to be noted that the positional relations between the UTb 26 and UTc 27, and between the UTd 28 and UTe 29 are reversed in even number lines and uneven number lines of the first straight running paths 47. The profile generator 81 stores the produced profile 82 in the RAM 62.

Although the breast is relatively smooth in shape and has less rough parts on the surface, there are differences in heights, as compared to other parts of the body, at boundary of the nipple, the under bust, the breast, the axillary cavity, and the area under the collarbone. Because of this, the selective drive of the UT may not be able to catch up with the movement of the UT unit 15, and some areas may not be subjected to the ultrasonic scanning. For example, when the UTa 25 is driven for the ultrasonic scanning until the border between the areas A1 and A2 as shown in FIG. 6 and the drive is switched to the UTb 26, the UT unit 15 at this time is located directly below the areas A1 and A2, and therefore the anterior half of the area A2 cannot be subjected to the ultrasonic scanning. To prevent this, the profile generator 81 sets the UT drive column of the profile 82 to switch the UTs for the next area before the border between the adjacent areas, and thereby minimizing the area not subjected to the ultrasonic scanning.

Referring back to FIG. 4, a transmitting/receiving section 64 is constituted of pulsar and receiver. Five transmitting/receiving sections 64 are provided for the UTa 25 to UTe 29 on a one-by-one basis. Among the UTa 25 to UTe 29, the transmitting/receiving section 64 makes the UT selected in the profile 82 transmit the ultrasonic wave and receive the echo wave under the control of the main controller 60 in synchronization with the movement of the UT unit 15 by the belt conveyor 17. For this configuration, the ultrasonic scanning is performed with different UT for each area driven according to the movement of the UT unit 15.

Based on the drive signal sent from the main controller 60, each transmitting/receiving section 64 sends exciting pulses to the UT selected in the profile 82 to generate the ultrasonic wave. In addition, the transmitting/receiving section 64 amplifies a detection signal output from the UT which received the reflected echo from the object C to be viewed, and applies A/D conversion to the detection signal. The detection signal digitized by the A/D conversion is output to an image processor 65.

Since the breast C1 has a convex shape, the distance between the object C to be viewed and the UT differs from area to area. The distance becomes further at the area under of the collarbone and the under bust, and the distance between the UT and the nipple is closest. The distance between the object C to be viewed and the UT can be obtained when the shape data is analyzed. The transmitting/receiving section 64 properly changes the drive condition (drive voltage and the like) of the UT according to the distance to the object C to be viewed, and thereby applying the ultrasonic wave with constant intensity to the object C to be viewed.

The image processor 65 performs orthogonal detection processing to the detection signal from the transmitting/receiving section 64, and converts the detection signal into complex baseband signal. The image processor 65 then generates an ultrasonic image by referring to the shape data from the detection signals obtained from several times of the transmissions and receptions of the ultrasonic waves and echoes while the UT 15 is moved from the running start point S to the running endpoint E of the belt conveyor 17. A display controller 66 merges patient information and/or examination information on the ultrasonic image generated in the image processor 65 and displays the merged image on a monitor 67.

The laser light source 37 of the shape measurement unit 16 and the motor 46 for driving the belt conveyor 17 are connected to the main controller 60. The main controller 60 controls the drive of the laser light source 37 and the motor 46. The main controller 60 detects the moved amount of each unit 15, 16 (position on the XY plane) on the belt conveyor 17 based on, for example, a drive pulse number input to the motor 46.

Figure 7:
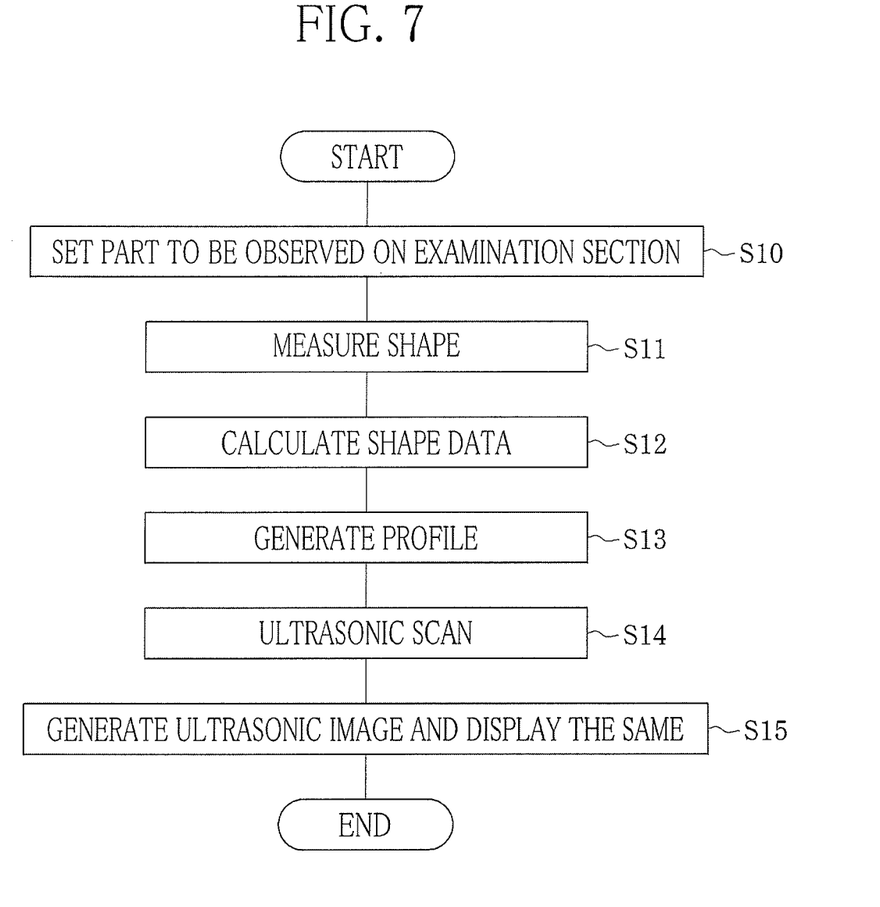
FIG. 7 is a flow chart illustrating a procedures of ultrasonic diagnosis.

Next, the procedures of the ultrasonic diagnosis on the object C to be viewed using the above-deceived ultrasonic diagnostic apparatus 2 are explained. First of all, the patient's body H is laid on her stomach on the bed, and kept quiet with the object C to be viewed is pushed against the elastic sheet 14 (S10). After information about the patient's body H, examination date, and the like are input by operating the operation section 63, the operation input signal instructing to start the examination is input. At this time, the belt conveyor 17 is stopped, and therefore the UT unit 15 and the shape measurement unit 16 are positioned at the running start point S.

Upon receipt of the operation input signal from the operation section 63, the main controller 60 drives the motor 46 to move each unit 15, 16 by the belt conveyor 17. While moving each unit 15, 16, the main controller 60 drives the laser light source 37. Owing to this, the laser light is applied to the object C to be viewed from the light projecting window 35, and the reflected light is received by the receiver 38 through the light receiving window 36 (S11). The shape data calculator 80 of the main controller 60 calculates shape data based on the output of the light receiver 38 (S12). Based on the shape data, the profile 82 is produced by the profile generator 81 (S13). The produced profile 82 is stored in the RAM 62.

After the shape measurement is completed, the main controller 60 keeps driving the belt conveyor 17 (motor 46) until each unit 15, 16 comes back from the running end point E to the running start point S after passing through the second straight running path 49. Once each unit 15, 16 comes back to the running start point S, the main controller 60 stops the drive of the motor 46.

The main controller 60 then drives the belt conveyor 17 again to move each unit 15, 16. While moving each unit 15, 16, the main controller 60 makes the UTs transmit the ultrasonic wave and receive the reflected echo by controlling the drive of the transmitting/receiving section 64 based on the profile 82 stored in the RAM 62 (S14). Owing to this, the UT corresponding to the shape of the object C to be viewed is selectively driven properly, and thus performing the transmission of the ultrasonic wave and the reception of the reflected echo in a vertical manner with respect to the object C to be viewed.

The detection signal output from the UT by the ultrasonic scanning is amplified in the transmitting/receiving section 64 to be subjected to the A/D conversion, and then subjected to the orthogonal detection in the image processor 65. The processed signal is then displayed as an ultrasonic tomographic image by the display controller 66 on the monitor 67.

As explained above, the UTa 25 to UTe 29 whose angles to the object C to be viewed are different from one another are used to perform the ultrasonic scanning by selectively driving the UT which could vertically emit the ultrasonic wave to the object C to be viewed based on the shape measurement result of the object C to be viewed. Owing to this, the ultrasonic image of high quality can be obtained with relatively small number of UTs, without proving a mechanism to lift up and down the UTs with respect to the object to be viewed.

Figure 8:
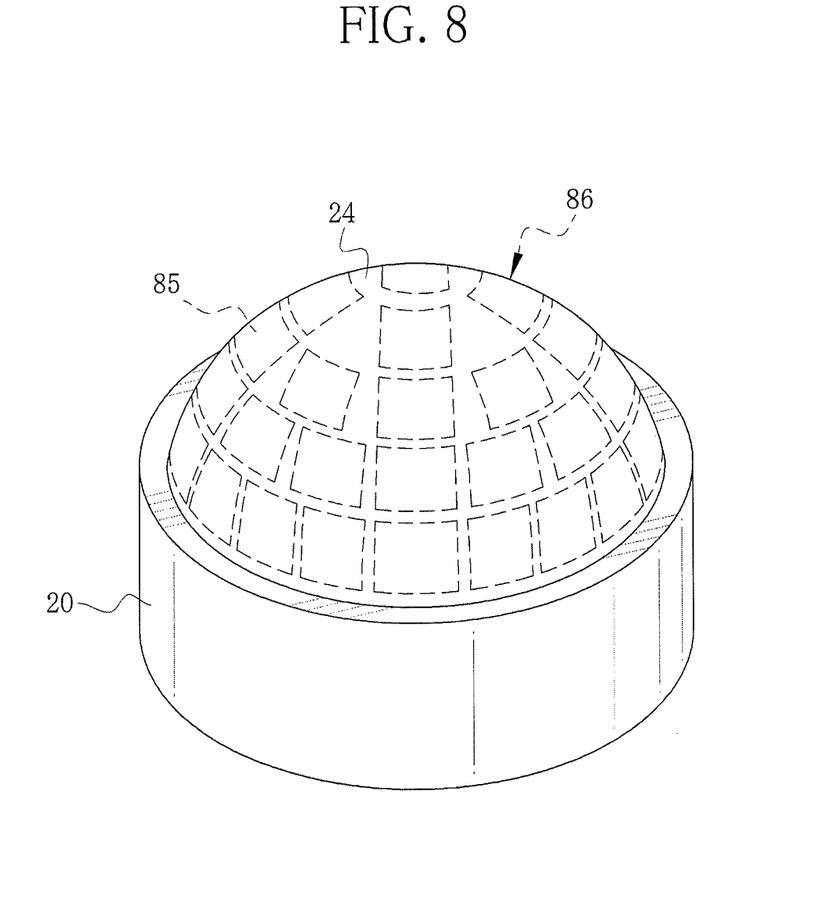
FIG. 8 is a perspective view illustrating another example of the ultrasonic transducer array.

In the above embodiment, the UT array 22 in which the UTs are arranged in one dimension is used as the example. In this case, the ultrasonic wave is applied vertically to the object to be viewed one-dimensionally in the X direction, and the tilt of the object to be viewed in the Y direction is not considered, and therefore the UT surface can not always be parallel to the surface of the object C to be viewed. To solve this problem, UT array 86 in which plural UTs 85 are arranged radially on a convex hemispherical surface, as shown in FIG. 8, may be used. The ultrasonic wave can be applied vertically to the object C to be viewed with higher precision by selectively driving the UT whose surface becomes parallel to the surface of the object C to be viewed. Components same as the UT array 22 are denoted by the same reference numerals and the explanations thereof are omitted.

The surface on which the UTs are arranged is not limited to the curved convex surface, as exemplified in the above embodiments, but may be the curved concave surface. If the UTs are arranged on the curved concave surface, however, the transmissions of the ultrasonic waves and the receptions of the reflected echoes may be distracted at the end of the curved surface depending of the shape thereof, and thus the curved convex surface is more preferable.

As to the shape of the breast, in general, the slope (inclination) from the area under the collarbone to the nipple is gentle, and the slope from the nipple to the under bust is relatively steep. In view of this, the surface on which the UTs are arranged can be formed noncentrosymmetry such that a surface with gentle slope and surface with steep slope to follow the shape of the breast are formed, instead of forming the surface centrally symmetric.

Moreover, the surface where the UTs are arranged is not limited to a smooth curved surface, but may have a multiangular shape in cross-section formed by connecting plural flat surfaces tilted by different angles. That is, the surface where the UTs are arranged can be in any form as long as the plural UTs constituting the UT array differ in angles.

In the above embodiments, although the PZT-based piezoelectric ceramic thick film is used as the material of the UT, the present invention is not limited to this. Semiconductor devices such as cMUT and pMUT, each of which produced on a silicon substrate employing the MEMS technique, may be used. With use of such semiconductor devices, the UT array can be minimized comparing the UT array using the piezoelectric ceramic thick film.

In the above embodiments, the ultrasonic scanning is performed after the shape measurement. However, it is possible that the ultrasonic scanning is performed while the shape measurement is performed. In addition, in the above embodiments, although the shape measurement unit is placed on the belt conveyor, the shape measurement unit may be buried at, for example, the corner or the center of a bottom surface of the water tank, as long as the laser light system is formed to scan with the later light using a movable reflection mirror and the like.

Instead of using the laser light source and the light receiver of the above embodiments, the UTs may be used as the shape measurement unit to calculate the shape data based on the detection signal obtained by the ultrasonic scanning using the specific UTs. For example, the UTa 25 whose angle formed with the XY plane is approximately 0 degree is driven to perform the ultrasonic scanning of the object C to be viewed. The shape measurement can be executed in the non contact manner like the above embodiments. The shape measurement is not limited to the non contact manner, but may be of contact manner made by contacting a pressure sensor and the like to the object C to be viewed.

The size, number, arrangement pitch, angle, and the like of the UTs may appropriately be changed according to the feature of the ultrasonic diagnostic apparatus 2. If the number of the UTs is increased, and the angle is adjusted more precisely, the ultrasonic scanning can be performed with more precision. The angle of each UT may be set based on the angle frequently appeared in the shape data of breast in the past.

It is also possible that the same number of UT units as the first straight running paths are prepared to perform the ultrasonic scanning simultaneously in all lines. At this time, each UT array is formed to have a size that the adjacent UT arrays do not contact with each other. If the belt conveyor is an endless belt, the curved running paths and the second straight running path is not needed, and the ultrasonic scanning can be made at short times.

The signal communication among the UTs, laser light source, light receiver, motor and processor may be made wirelessly.

The object to be viewed is not limited to the breast, but may be other body parts including soft tissue, such as abdomen, thyroid gland, carotid artery and joints (elbow, knee, etc.).

Various changes and modifications are possible in the present invention and may be understood to be within the present invention.

What is claimed is:

1. An ultrasonic diagnostic apparatus comprising:
a shape measurement section for measuring a shape of an object to be viewed of a subject;
an ultrasonic transducer array including a plurality of ultrasonic transducers arranged on a curved surface, each ultrasonic transducer transmitting an ultrasonic wave to said object to be viewed and receiving an echo of the ultrasonic wave from said object to be viewed;
a moving mechanism for moving said ultrasonic transducer array only two dimensionally; and
a drive controller for selectively driving an ultrasonic transducer which applies the ultrasonic wave at an angle closest to vertical with respect to the object to be viewed among the plurality of said ultrasonic transducers according to the moved position of said ultrasonic transducer array, based on the shape information of said object to be viewed obtained by said shape measurement section.

2. The ultrasonic diagnostic apparatus according to claim 1, wherein the plurality of said ultrasonic transducers of said ultrasonic transducer array is arranged on a curved convex surface or a curved concave surface.

3. The ultrasonic diagnostic apparatus according to claim 2, wherein said shape measurement section measures the shape of said object to be viewed in a noncontact manner.

4. The ultrasonic diagnostic apparatus according to claim 3, wherein said shape measurement section includes a light projector for applying light to said object to be viewed and a light receiver for receiving the reflected light from said object to be viewed, and calculates shape information of said object to be viewed based on an output of said light receiver.

5. The ultrasonic diagnostic apparatus according to claim 4, wherein said light projector and said light receiver are disposed along a conveying path with said ultrasonic transducers, wherein when said moving mechanism moves the ultrasonic transducer array, the light projector and light receiver move ahead of said ultrasonic transducers.

6. The ultrasonic diagnostic apparatus according to claim 4, wherein said ultrasonic transducer is a semiconductor device.

7. The ultrasonic diagnostic apparatus according to claim 6, wherein said semiconductor device is a cMUT (capacitive micromachined ultrasonic transducer) or a pMUT (piezoelectric micromachined ultrasonic transducer).

8. The ultrasonic diagnostic apparatus according to claim 6, wherein an ultrasonic wave transmission medium is mediated between said object to be viewed and said ultrasonic transducer array.

9. The ultrasonic diagnostic apparatus according to claim 4, further comprising:
   a water tank for storing liquid, said ultrasonic transducers moving in said water tank; and
   an elastic sheet for covering a surface of said liquid, said subject being made into contact with said elastic sheet.

10. The ultrasonic diagnostic apparatus according to claim 9, wherein said light projector and said light receiver are placed inside said water tank and are disposed along a conveying path with said ultrasonic transducers, wherein when said moving mechanism moves the ultrasonic transducer array, the light projector and light receiver move ahead of said ultrasonic transducers.

11. The ultrasonic diagnostic apparatus according to claim 1, wherein said object to be viewed includes a soft tissue.

* * * * *